(12) United States Patent
Chew et al.

(10) Patent No.: US 8,195,262 B2
(45) Date of Patent: *Jun. 5, 2012

(54) SWITCH-MODE OXIMETER LED DRIVE WITH A SINGLE INDUCTOR

(75) Inventors: Bradford B. Chew, San Ramon, CA (US); Ethan Petersen, Castro Valley, CA (US); William Shea, Livermore, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1665 days.

This patent is subject to a terminal disclaimer.

(21) Appl. No.: 11/494,394

(22) Filed: Jul. 26, 2006

(65) Prior Publication Data

US 2006/0264720 A1    Nov. 23, 2006

Related U.S. Application Data

(63) Continuation of application No. 10/787,852, filed on Feb. 25, 2004, now Pat. No. 7,120,479.

(51) Int. Cl.
*A61B 5/1455* (2006.01)
*H05B 37/00* (2006.01)
(52) U.S. Cl. .......... 600/323; 600/310; 315/186
(58) Field of Classification Search .......... 600/310, 600/323; 315/186, 313; 356/41
See application file for complete search history.

(56) References Cited

U.S. PATENT DOCUMENTS

| | | |
|---|---|---|
| 3,638,640 A | 2/1972 | Shaw |
| 4,714,341 A | 12/1987 | Hamaguri et al. |
| 4,742,294 A | 5/1988 | Gallios |
| 4,802,486 A | 2/1989 | Goodman et al. |
| 4,805,623 A | 2/1989 | Jöbsis |
| 4,807,631 A | 2/1989 | Hersh et al. |
| 4,911,167 A | 3/1990 | Corenman et al. |
| 4,913,150 A | 4/1990 | Cheung et al. |
| 4,928,692 A | 5/1990 | Goodman et al. |
| 4,934,372 A | 6/1990 | Corenman et al. |
| 4,936,679 A | 6/1990 | Mersch |
| 4,938,218 A | 7/1990 | Goodman et al. |
| 4,945,332 A * | 7/1990 | Sakamoto et al. .............. 336/69 |
| 4,971,062 A | 11/1990 | Hasebe et al. |
| 4,972,331 A | 11/1990 | Chance |
| 4,974,591 A | 12/1990 | Awazu et al. |
| 5,028,787 A | 7/1991 | Rosenthal et al. |

(Continued)

FOREIGN PATENT DOCUMENTS

GB    2044550 A    10/1980

(Continued)

OTHER PUBLICATIONS

International Search Report dated Sep. 12, 2007; 12 pages.

*Primary Examiner* — Eric Winakur

(57) ABSTRACT

A light emitter drive circuit for an oximeter which utilizes a single inductor for driving multiple light emitters. The inductor is connected to a switching circuit to multiple energy storage circuits, such as capacitors. These are alternately charged up, using the same inductor. Subsequently, the capacitors are alternatively discharged for their corresponding light emitters through the same inductor. Also, the magnetic susceptibility of the LED drive circuit is reduced by using magnetic flux canceling in the inductor. In one embodiment, a toroidal inductor is used with geometric symmetry and its magnetic flux. In other embodiment, a dual core closed bobbin shielded inductor is used.

27 Claims, 3 Drawing Sheets

U.S. PATENT DOCUMENTS

| | | | |
|---|---|---|---|
| 5,065,749 A | 11/1991 | Hasebe et al. |
| 5,084,327 A | 1/1992 | Stengel |
| 5,119,815 A | 6/1992 | Chance |
| 5,122,974 A | 6/1992 | Chance |
| 5,165,162 A | 11/1992 | Charles et al. |
| 5,167,230 A | 12/1992 | Chance |
| 5,190,038 A | 3/1993 | Polson et al. |
| 5,227,676 A | 7/1993 | Bahr et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,297,548 A | 3/1994 | Pologe |
| 5,351,685 A | 10/1994 | Potratz |
| 5,355,880 A | 10/1994 | Thomas et al. |
| 5,368,026 A | 11/1994 | Swedlow et al. |
| 5,372,136 A | 12/1994 | Steuer et al. |
| 5,385,143 A | 1/1995 | Aoyagi |
| 5,390,670 A | 2/1995 | Centa et al. |
| 5,413,099 A | 5/1995 | Schmidt et al. |
| 5,469,845 A | 11/1995 | DeLonzor et al. |
| 5,482,036 A | 1/1996 | Diab et al. |
| 5,483,646 A | 1/1996 | Uchikoga |
| 5,553,614 A | 9/1996 | Chance |
| 5,564,417 A | 10/1996 | Chance |
| 5,575,285 A | 11/1996 | Takanashi et al. |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,662,106 A | 9/1997 | Swedlow et al. |
| 5,680,857 A | 10/1997 | Pelikan et al. |
| 5,692,503 A | 12/1997 | Kuenstner |
| 5,713,355 A | 2/1998 | Richardson et al. |
| 5,730,124 A | 3/1998 | Yamauchi |
| 5,746,697 A | 5/1998 | Swedlow et al. |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,803,910 A | 9/1998 | Potratz |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,871,442 A | 2/1999 | Madarasz et al. |
| 5,873,821 A | 2/1999 | Chance et al. |
| 5,920,263 A | 7/1999 | Huttenhoff et al. |
| 5,921,921 A | 7/1999 | Potratz et al. |
| 5,924,979 A | 7/1999 | Swedlow et al. |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,064,898 A | 5/2000 | Aldrich |
| 6,081,742 A | 6/2000 | Amano et al. |
| 6,088,607 A | 7/2000 | Diab et al. |
| 6,120,460 A | 9/2000 | Abreu |
| 6,134,460 A | 10/2000 | Chance |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,198,405 B1 | 3/2001 | Anderson et al. |
| 6,226,539 B1 | 5/2001 | Potratz |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,298,252 B1 | 10/2001 | Kovach |
| 6,312,393 B1 | 11/2001 | Abreu |
| 6,353,750 B1 | 3/2002 | Kimura et al. |
| 6,397,091 B2 | 5/2002 | Diab et al. |
| 6,411,045 B1 | 6/2002 | Nerone |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Pishney et al. |
| 6,658,277 B2 | 12/2003 | Wasserman |
| 6,662,030 B2 | 12/2003 | Khalil et al. |
| 6,665,551 B1 | 12/2003 | Suzuki |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,707,257 B2 | 3/2004 | Norris |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,731,274 B2 | 5/2004 | Powell |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,829,496 B2 | 12/2004 | Nagai et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,897,754 B2 | 5/2005 | Jeong et al. |
| 6,898,451 B2 | 5/2005 | Wuori |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,993,371 B2 | 1/2006 | Kiani et al. |
| 6,996,427 B2 | 2/2006 | Ali et al. |
| 7,006,865 B1 | 2/2006 | Cohen |
| 7,024,235 B2 | 4/2006 | Melker et al. |
| 7,027,849 B2 | 4/2006 | Al-Ali |
| 7,030,749 B2 | 4/2006 | Al-Ali |
| 7,035,697 B1 | 4/2006 | Brown |
| 7,047,056 B2 | 5/2006 | Hannula et al. |
| 7,120,479 B2 | 10/2006 | Chew |
| 7,127,278 B2 | 10/2006 | Melker et al. |
| 7,162,306 B2 | 1/2007 | Caby et al. |
| 7,209,775 B2 | 4/2007 | Bae et al. |
| 7,236,811 B2 | 6/2007 | Schmitt |
| 7,263,395 B2 | 8/2007 | Chan et al. |
| 7,272,426 B2 | 9/2007 | Schmid |
| 7,373,193 B2 | 5/2008 | Al-Ali et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |

| | | |
|---|---|---|
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0064024 A1 | 3/2006 | Schnall |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2006/0264720 A1 | 11/2006 | Chew |

FOREIGN PATENT DOCUMENTS

| | | |
|---|---|---|
| JP | 6098881 | 4/1994 |
| JP | 9192120 | 7/1997 |
| JP | 2004290412 | 10/2004 |

* cited by examiner

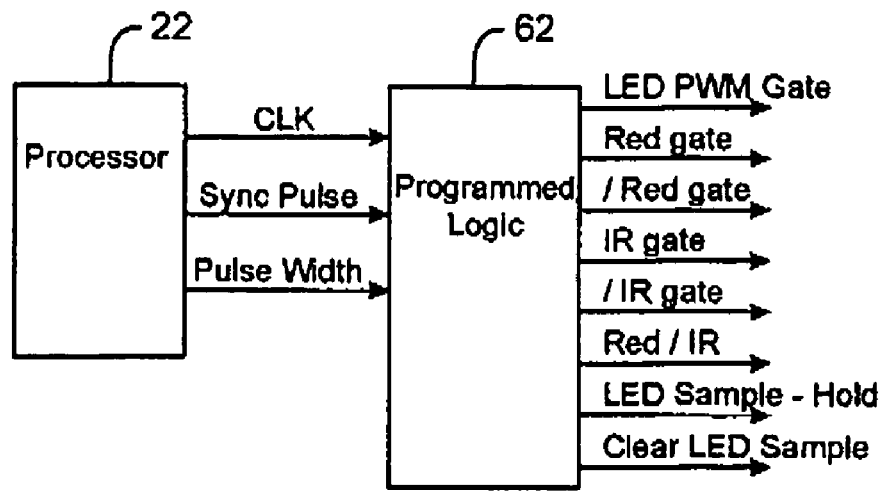
FIG. 3
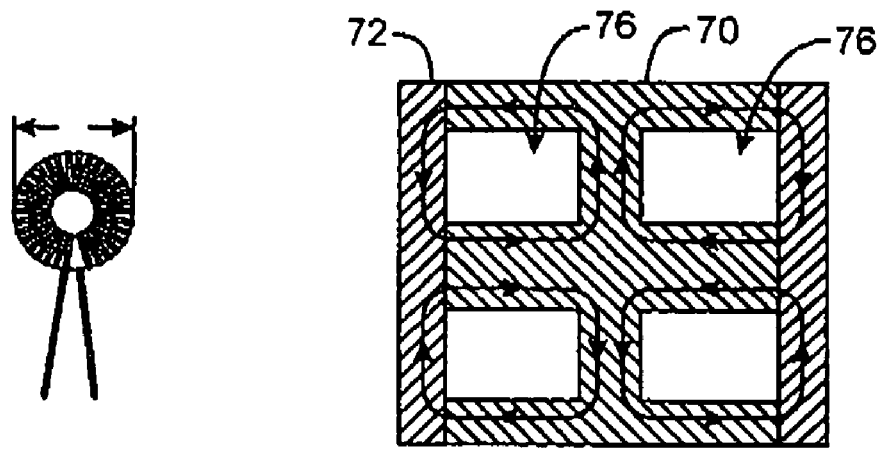
FIG. 4
FIG. 5
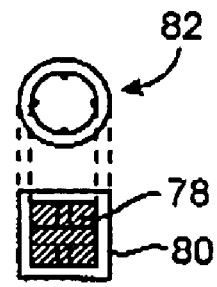
FIG. 6

SWITCH-MODE OXIMETER LED DRIVE WITH A SINGLE INDUCTOR

CROSS-REFERENCE TO RELATED APPLICATIONS

This application is a continuation of U.S. application Ser. No. 10/787,852, filed on Feb. 25, 2004.

BACKGROUND OF THE INVENTION

The present invention relates to oximeters, and in particular to LED drive circuits in pulse oximeters.

Pulse oximetry is typically used to measure various blood chemistry characteristics including, but not limited to, the blood-oxygen saturation of hemoglobin in arterial blood, the volume of individual blood pulsations supplying the tissue, and the rate of blood pulsations corresponding to each heartbeat of a patent. Measurement of these characteristics has been accomplished by use of a non-invasive sensor which scatters light through a portion of the patient's tissue where blood perfuses the tissue, and photoelectrically senses the absorption of light in such tissue. The amount of light absorbed at various wavelengths is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

The light sources, typically light emitting diodes (LEDs), need to be driven with current to activate them. Because of the significant amount of current required, this can interfere with reducing power consumed by an oximeter. One solution is shown in U.S. Pat. No. 6,226,539. There, an inductor and capacitor circuit is used to first store charge in a first switch position, and then subsequently, in a second switch position, deliver that stored charge to the LED. Two different inductor and capacitor circuits are used, one for each LED. It would be desirable to reduce the number of components required in the circuit of this patent.

BRIEF SUMMARY OF THE INVENTION

The present invention provides a light emitter drive circuit for an oximeter which utilizes a single inductor for driving multiple light emitters. The inductor is connected through a switching circuit to multiple energy storage circuits, such as capacitors. These are alternately charged up, using the same inductor. Subsequently, the capacitors are alternately discharged to activate their corresponding light emitters through the same inductor.

In another aspect of the present invention, the magnetic susceptibility of the LED drive circuit is reduced by using magnetic flux canceling in the inductor. In one embodiment, a toroidal inductor is used with geometric symmetry in its magnetic flux. In another embodiment, a dual core closed bobbin shielded inductor is used. This embodiment has windings of both cores in series that are used to cancel the effect of an external magnetic field.

For a further understanding of the nature and advantages of the present invention, reference should be made to the following description taken in conjunction with the accompanying drawings.

BRIEF DESCRIPTION OF THE DRAWINGS

FIG. 3 is a block diagram of one embodiment of the logic for generating the timing and control signals for the circuit of FIG. 2.

FIG. 4 is a diagram of a toroidal inductor used in one embodiment of the present invention.

FIGS. 5 and 6 are diagrams of a dual core inductor according to an embodiment of the present invention.

DETAILED DESCRIPTION OF THE INVENTION

Oximeter System

Figure 1:
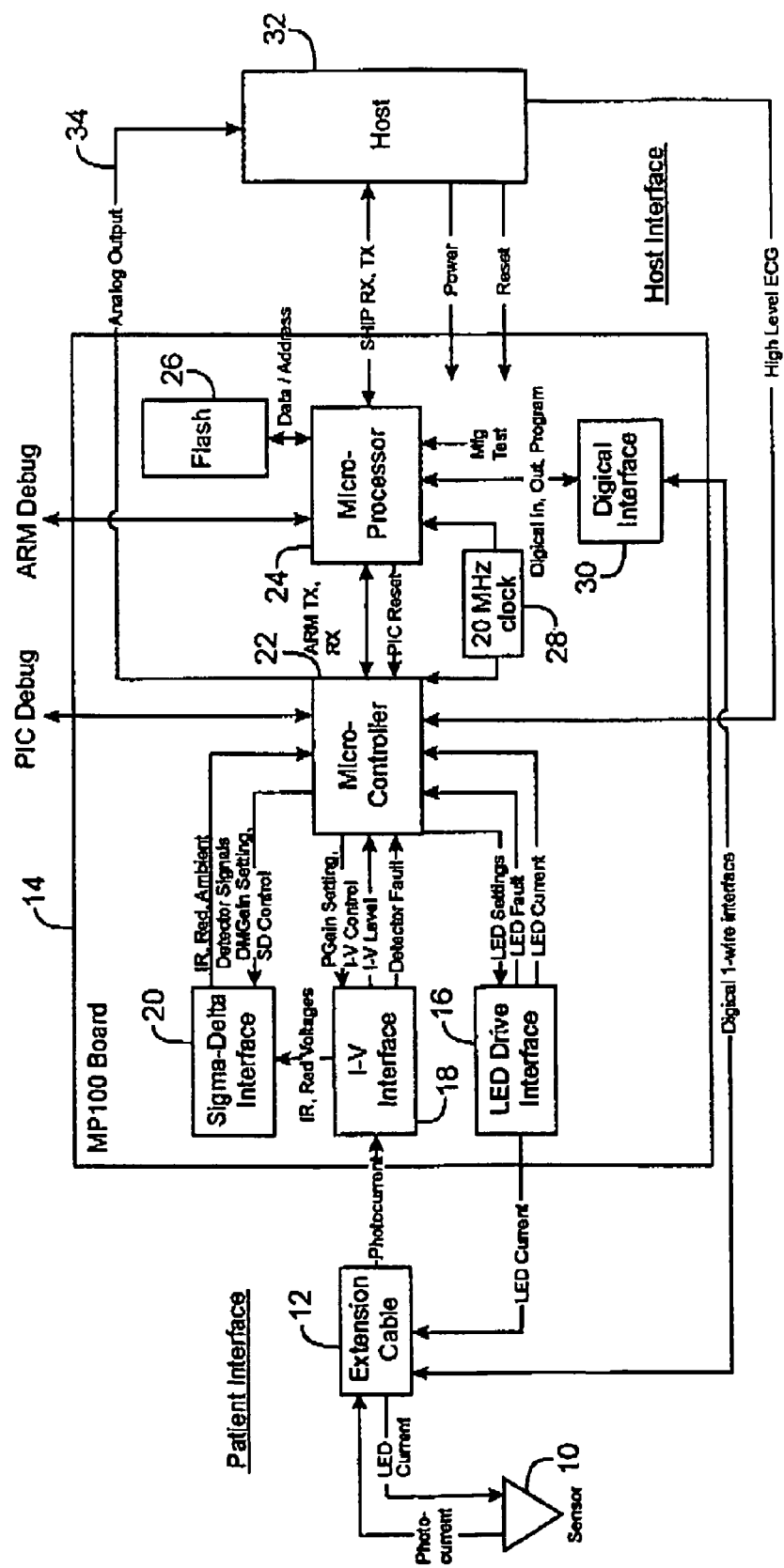
FIG. 1 is a block diagram of an oximeter incorporating the present invention.

FIG. 1 illustrates an embodiment of an oximetry system incorporating the present invention. A sensor 10 includes red and infrared LEDs and a photodetector. These are connected by a cable 12 to a board 14. LED drive current is provided by an LED drive interface 16. The received photocurrent from the sensor is provided to an I-V interface 18. The IR and red voltages are then provided to a sigma-delta interface 20 incorporating the present invention. The output of sigma-delta interface 20 is provided to a microcontroller 22. Microcontroller 22 includes flash memory for a program, and SRAM memory for data. The processor also includes a microprocessor chip 24 connected to a flash memory 26. Finally, a clock 28 is used and an interface 30 to a digital calibration in the sensor 10 is provided. A separate host 32 receives the processed information, as well as receiving an analog signal on a line 34 for providing an analog display.

LED Drive Circuit

Figure 2:
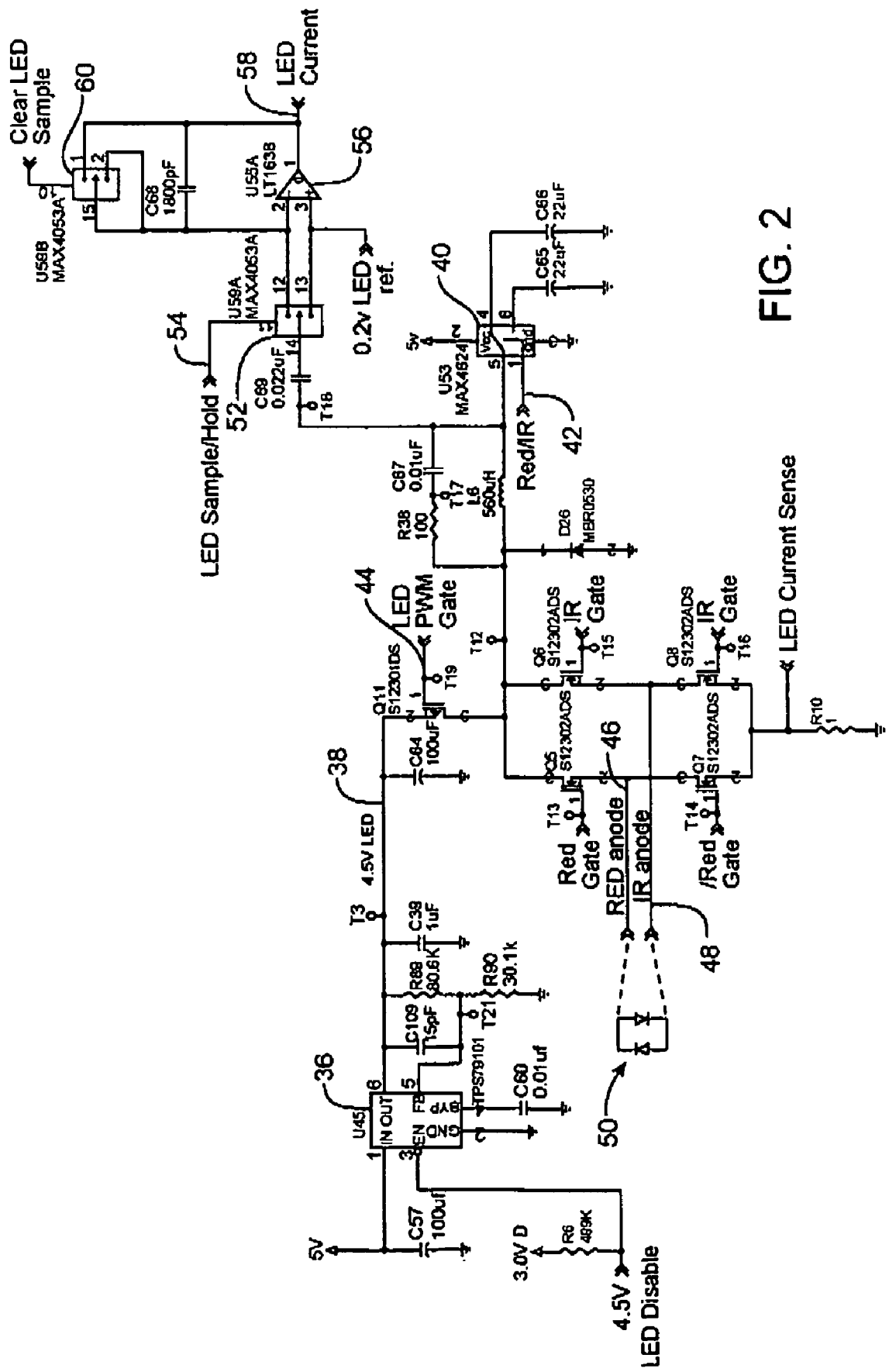
FIG. 2 is a circuit diagram of a LED drive circuit according to an embodiment of the present invention.

FIG. 2 is a circuit diagram of the LED drive circuit according to an embodiment of the invention, which forms a portion of LED drive interface 16 of FIG. 1. A voltage regulator 36 provides a voltage separate from the voltage supply for the overall oximeter circuitry. The output is provided as a 4.5 volt signal on line 38, with the level being set by the feedback resistor divider of resistors R89 and R90. The voltage on line 38 is provided to a FET transistor Q11 to an inductor L6. The current through inductor L6 is provided by a switch 40 to one of capacitors C65 and C66, which store charge for the red and IR LEDs, respectively. A red/IR control signal on line 42 selects the switch position under control of the oximeter processor. A control signal LED PWM gate on line 44 controls the switching of transistor switch Q11.

Once the capacitors are charged up, the control signal on line 44 turns off switch Q11 and current is provided from either capacitor C65 or C66, through switch 40 and inductor L6 to either the red anode line 46 or the IR anode line 48 by way of transistors Q5 and Q6, respectively. A signal "red gate" turns on transistor Q5, while its inverse, "/red gate" turns off transistor Q7. This provides current through the red anode line 46 to the back to back LEDs 50, with the current returning through the IR anode to transistor Q8 and through resistor R10 to ground. Transistor Q8 is turned on by the signal "/IR gate" while the inverse of this signal, "IR gate" turns off transistor Q6. The signals are reversed when the IR anode is to be driven, with the "IR gate" and "red gate" signals, and their inverses, changing state, so that current is provided through transistor Q6 to IR anode 48 and returns through red anode 46 and through transistor Q7 to resistor R10 and ground. The "LED current sense" signal is read for calibration purposes not relevant to the present invention.

When the current from the capacitor C65 or C66 is provided through inductor L6 to the LEDs, and that current is switched off at the desired time, transistor Q11 is turned on so that the remaining current during the transition can be dumped into capacitor C64. This addresses the fact that the FET transistor switching is not instantaneous. Subsequently, C64 will dump its current through Q11 and inductor L6 into the capacitors when they are recharged.

Resistor R38 and capacitor C67 are connected in parallel to inductor L6 to protect against signal spikes, and provide a smooth transition. Connected to inductor L6 is a sampling circuit with a switch 52 controlled by an LED sample hold signal on line 54 to sample the signals and provide them through an amplifier 56 to a "LED current" signal on line 58 which is read by the processor. Operational amplifier 56 operates between 4.5 volts and ground. Thus, a voltage reference slightly above ground, of 0.2 volts, is provided as a voltage reference on pin 3. An integrating capacitor C68 is provided in parallel to amplifier 56. A switch 60 responds to a "clear LED sample" signal to operate the switch to short out the capacitor between samples.

The sample and hold circuit measures the voltage at node T18, between capacitor C69 and inductor L6, to determine the current. Capacitor C69 is $\frac{1}{1000}$ of the value of capacitors C65 and C66. Thus, a proportional current is provided through C69, which is injected through switch 52 to integrating capacitor C68 to provide a voltage which can be measured at the output of amplifier 56 on line 58. The voltage measured by the processor on line 58 is used as a feedback, with the processor varying the width of the pulse delivered to transistor Q11 to selectively vary the amount of energy that's delivered to the capacitors 65 and 66, and then is eventually discharged to the LEDs 50. A PI (Proportional Integral) loop inside the processor then controls the PWM signal at Q11. This allows precise control of the LED intensity, allowing it to be maximized, if desired, without exceeding the desired limits (to avoid burning the patent, etc.).

The lower left of the diagram shows a "4.5 v LED disable" signal which is used by the microprocessor to turn off the voltage regulator 36 in certain instances. For example, diagnostics looking for shorts in a new sensor plugged in will turn off the voltage regulator if there is a problem with the LED line.

FIG. 3 illustrates processor 22, from FIG. 1, connected to programmed logic 62, which is in the LED drive interface 16 in FIG. 1. Programmed logic 62 provides the different control signals used by the circuit of FIG. 2 in response to basic timing signals from the processor of a clock, a sync pulse, and a pulse width signal.

Thus, the present invention provides an improvement over the circuit shown in U.S. Pat. No. 6,226,539 by moving the switch position between the inductor and the capacitors to eliminate the need for two inductors. This not only reduces the part count, requiring only one inductor instead of two, but also provides better matching between the red and IR drive currents since both use the same inductor.

In another aspect of the invention, the LED drive circuit's susceptibility to magnetic interference is reduced. This magnetic interference can distort the detected pleth waveform. This is minimized by using magnetic flux canceling in the inductor. In one embodiment, this is a toroidal inductor as shown in FIG. 4. The toroidal inductor has a geometric symmetry in its magnetic flux. Another embodiment uses a dual core closed bobbin shielded inductor, such as shown in FIGS. 5 and 6. The windings of both cores in series are used to cancel the effect of an external magnetic field. These magnetic flux canceling inductors can be used either in the circuit of FIG. 2, or could be used in the dual inductor embodiment of the prior art. FIG. 5 shows the dual core inductor with a bobbin 70 in a cylinder 72. The wires are wound through gaps 76, as shown in FIG. 6. A first winding 78 is clockwise, while a second winding 80 is counterclockwise. A top view 82 is also shown. Ideally, the combined inductance in one embodiment is 680 uH.

The invention as illustrated in the embodiment of FIG. 2 enables the multiplexing of current, through an H-bridge topology, to back-to-back LEDs. Alternately, a different number of loads could be provided. The present invention is scalable to N-loads. The present invention is scalable to N-loads. The present invention provides significant efficiencies through reduction of support components, choice of components, and the properties of "loss-less" capacitor and inductor storage devices. The circuit of FIG. 2 can handle a range of forward voltage drops across the LEDs. The voltage provided varies automatically in accordance with the LED voltage drop, and does not put out more energy than it needs to.

The circuit is dynamically controlled through a PI loop in the processor, with current feedback being provided by the capacitive current divider from each storage capacitor (C65 and C66), which provides isolation. The feedback can be calibrated with a traditional in-line sense resistor, R10. In addition, this technique allows adjustment of the peak current for optimal signal-to-noise during the sampling period.

The addition of the upstream linear regulator 36 enhances power supply rejection capability, while the PI loop provides additional power supply insensitivity (to draft, P-P, surge, etc.).

As will be appreciated by those with skill in the art, the present invention can be embodied in other specific forms without department from the essential characteristics thereof. For example, instead of two drive lines, three drive lines could be provided by adding another leg with FET transistor switches connected to the inductor. Additionally, this could be scalable to more than three legs connected in parallel, similar to the leg of Q6, Q8, and the leg of Q5, Q7. Accordingly, the foregoing description is intended to be illustrative, but not limiting, of the scope of the invention which is set forth in the following claims.

We claim:

1. A light emitter drive circuit for an oximeter comprising:
   a voltage generating circuit;
   an inductor coupled to the voltage generating circuit;
   a first switching circuit coupled to a first node of the inductor;
   first and second energy storage circuits connected to the first switching circuit, such that current from the inductor can be steered by the first switching circuit to one of the energy storage circuits;
   a second switching circuit coupled to a second node of the inductor; and
   first and second light emitter drive lines connected to the second switching circuit, such that energy from the first and second energy storage circuits can be alternately coupled to the first and second light emitter drive lines.

2. The circuit of claim 1 wherein the first and second energy storage circuits comprise first and second capacitors.

3. The circuit of claim 1 wherein the voltage generating circuit is a voltage regulator separate from a supply voltage for a remainder of the oximeter.

4. The circuit of claim 1 comprising a resistor and a capacitor in parallel with the inductor.

5. The circuit of claim 1 wherein the inductor is a magnetic flux canceling inductor.

6. The circuit of claim 5 wherein the inductor is a torodial inductor.

7. The circuit of claim 5 wherein the inductor is a dual core closed bobbin shielded inductor.

8. The circuit of claim 1 comprising a sample and hold circuit connected to the second node of the inductor.

9. The circuit of claim 1 comprising at least a third energy storage circuit connected to the first switching circuit, such that current from the inductor can be steered by the first switching circuit to one of the energy storage circuits.

10. A light emitter drive circuit for an oximeter comprising:
a voltage generating circuit;
first and second energy storage circuits;
a magnetic flux canceling inductor coupled to the voltage generating circuit; and
switching circuitry including an element disposed between the inductor and the first and second energy storage circuits, wherein the switching circuitry is configured to first steer current passing through the inductor into the energy storage circuits, and then provide energy from the first and second energy storage circuits back through the inductor to drive lines for light emitters.

11. A method comprising:
directing electrical current through an inductor in a first direction to an energy storage device;
storing energy in the energy storage device, wherein storing energy in the energy storage device comprises coupling the energy storage device to the inductor using a switching device;
directing electrical current from the energy storage device through the inductor in a second direction; and
providing a drive signal to a light emitter drive line, wherein the drive signal comprises the electrical current in the second direction.

12. The method of claim 11 wherein directing electrical current through the inductor in a first direction comprises coupling the inductor to a voltage generating source.

13. The method of claim 11 wherein directing energy through the inductor in a second direction comprises uncoupling the inductor from a voltage generating source.

14. The method of claim 11 wherein coupling the energy storage device to the inductor using the switching device comprises alternately coupling a first energy storage device and a second energy storage device to the inductor.

15. The method of claim 11 wherein providing the drive signal to the light emitter drive line comprises alternately providing the drive signal to a red light emitting diode and an infrared light emitting diode using switches.

16. The method of claim 11 comprising using a magnetic flux canceling inductor.

17. The method of claim 16 wherein the magnetic flux canceling inductor comprises a torodial inductor.

18. The method of claim 16 wherein the magnetic flux canceling inductor comprises a dual core bobbin shielded inductor.

19. A method of manufacture comprising:
providing a switch to couple a voltage generating circuit to an inductor;
coupling a first node of the inductor to a first switching circuit and a second node of the inductor to a second switching circuit;
configuring the first switching circuit to alternately connect with a first energy storage device and a second energy storage device; and
configuring the second switching circuit to alternately supply power to a first light emitting drive line and a second light emitting drive line.

20. A system comprising:
a sensor comprising a first light emitter drive line and a second light emitter drive line;
a board electrically coupled to the sensor, the board comprising:
a voltage generating circuit;
an inductor coupled to the voltage generating circuit;
a first switching circuit coupled to a first node of the inductor;
first and second energy storage circuits connected to the first switching circuit, such that current from the inductor can be steered by the first switching circuit to one of the energy storage circuits;
a second switching circuit coupled to a second node of the inductor, the second switching circuit connected to the first and second light emitter drive lines such that energy from the first and second energy storage circuits can be alternately coupled to the first and second light emitter drive lines.

21. The circuit of claim 20 wherein the first and second energy storage circuits comprise first and second capacitors.

22. The circuit of claim 20 wherein the voltage generating circuit is a voltage regulator separate from a supply voltage for a remainder of the system.

23. The circuit of claim 20 comprising a resistor and a capacitor in parallel with the inductor.

24. The circuit of claim 20 wherein the inductor comprises a magnetic flux canceling inductor.

25. The circuit of claim 24 wherein the inductor comprises a torodial inductor.

26. The circuit of claim 24 wherein the inductor comprises a dual core closed bobbin shielded inductor.

27. The circuit of claim 20 comprising a sample and hold circuit connected to the second node of the inductor.

\* \* \* \* \*